United States Patent
Yao et al.

(10) Patent No.: US 8,202,222 B2
(45) Date of Patent: Jun. 19, 2012

(54) EQUAL PHASE TWO-DIMENSIONAL ARRAY PROBE

(75) Inventors: Jinzhong Yao, Shenzhen (CN);
Wenping Zhou, Shenzhen (CN);
Zhiqiang Chen, Shenzhen (CN)

(73) Assignee: Sonoscape, Inc., Shenzhen (CN)

( * ) Notice: Subject to any disclaimer, the term of this patent is extended or adjusted under 35 U.S.C. 154(b) by 1250 days.

(21) Appl. No.: 11/975,091

(22) Filed: Oct. 16, 2007

(65) Prior Publication Data
US 2009/0099454 A1    Apr. 16, 2009

Related U.S. Application Data

(60) Provisional application No. 60/855,103, filed on Oct. 27, 2006.

(51) Int. Cl.
*A61B 8/00* (2006.01)

(52) U.S. Cl. ............... 600/459
(58) Field of Classification Search .......... 600/459, 600/437
See application file for complete search history.

(56) References Cited

U.S. PATENT DOCUMENTS

| 5,526,325 | A | * | 6/1996 | Sullivan et al. ......... 367/138 |
| 5,902,241 | A | * | 5/1999 | Seyed-Bolorforosh et al. ......... 600/443 |
| 6,375,617 | B1 | * | 4/2002 | Fraser ......... 600/443 |

* cited by examiner

*Primary Examiner* — Jacqueline Cheng
(74) *Attorney, Agent, or Firm* — Workman Nydegger

(57) ABSTRACT

An ultrasonic image scanning system for scanning an organic object includes a 2D array probe constructed with transducer elements in both azimuth and elevation dimension. There is a multiplexer disposed in one dimension to route the transducer elements to system front-end channels, while the other dimension can sum into the first dimension with various element number.

16 Claims, 6 Drawing Sheets

EQUAL PHASE TWO-DIMENSIONAL ARRAY PROBE

This Formal Application claims a Priority date of Oct. 27, 2006 benefited from a Provisional Application 60/855,103, filed by the same Applicants of this Patent Application. The disclosures made in the Provisional Application 60/855,103 are hereby incorporated by reference in this Application.

FIELD OF THE INVENTION

This invention generally relates to system and method for carrying out a medical imaging process with an improved method and configuration for arranging 3D imaging transducers. More particularly, this invention relates to an improved imaging acquisition method of arranging two-dimensional transducers for improving the volume image acquisition and convenience of probe production.

BACKGROUND OF THE INVENTION

Even though there are great advancements made in the image display technologies such that scanning images can be displayed with higher resolutions and can be viewed in 3D image from different angles to perform more accurate diagnoses. However, the processes of implementing the two-dimensional array probes are still limited by the technical difficulties. One example is the sparse two-dimensional array probe as disclosed in U.S. Pat. No. 5,911,692 and 6,014,897, that generates images of poor beam resolution and that further complicates the image construction processes by applying the transducer data.

The conventional one-dimensional (1D) array probe is arranged in either a linear flat or a curve convex configuration that has been employed in the ultrasound imaging application for years. The image generated by applying the echo data received from the probe is presented as a 2D cross section. The operator can move the probe around to acquire many two-dimensional image slices, and then interpolate these two-dimensional image slices to detect the disease. Some system also provides volume-rendering algorithm for the free hand or motor driven 3D acquisition for carrying out a pathological diagnosis. However, hand movements often introduce signal noises and measurement instability and lead to inaccurate image reconstruction and unreliable diagnoses.

Referring to FIG. 1A for a conventional beam former control for a one-dimensional (1D) array probe. The focusing acoustic beam is controlled to move along a beam scan direction aligned with the element direction to create a two dimensional (2D) image. A timing control circuit (not shown) generates signals for inputting to a time-delay profile generator as shown in FIGS. 1B, and 1C. The delayed transmit pulses are transmitted to the probe elements to emit the ultrasonic waves for transmitting, focusing, and then receiving the reflected signals transmitted through the similar delay profile to form a 1-D image. The beam can be scanned along the element direction with the same profile in linear array, or steered at different angle in phase array configuration to form a 2-D image.

In the past 10 years, many researchers tried the 'sparse' 2D array concept. It connects certain number of the 2D array element (e.g. 64×64=4096) into the current system beam forming channels (normally ranges from 64 to 256) with different distribution patterns. This can eliminate the need of a 4096-channel beam former in the ultrasound system. However, the beam resolution in this arrangement will be degraded badly in both azimuth and elevation direction with a significant channel reduction.

In U.S. Pat. No. 5,911,692 entitled "Sparse Two-dimensional Wideband Ultrasound Transducer Arrays", an ultrasonic imaging system is disclosed. The ultrasonic imaging system employs a thinned array of transducer elements in order to reduce the number of signal processing channels. The transducer elements are reduced in number and then selectively located at grid positions in a pattern, which reduces the side-lobe levels produced by the array. Thinning is accomplished by discretizing the aperture of the transducer array in two steps. First, a continuous aperture is discretized as a set of concentric rings. Then each ring is replaced by a set of spaced transducer elements.

FIG. 1D shows a sparse transducer array 10 disclosed by U.S. Pat. No. 5,911,892 that includes a plurality of transducer elements 12 driven by the transmitter 22. The ultrasonic energy reflected back from the scanned object is converted to an electrical signal by each receiving transducer and applied separately to a receiver through a set of transmit/receive (T/R) switches 26. The digital controller 28 receives command from a human operator to operate the transmitter 22, receiver 24 and switches 26. The controller 28 controls the switches 26 to turn on the transmitter for each of the transducer elements 12. The controller 28 further controls the switches to turn on the transmitter to receive the echo signals at different transducer element with appropriate time delay. The echo signals received by the receiver 24 are then amplified to generate a scan image. However, as discussed above, the sparse 2-D array scanning process cannot provide sufficient resolutions due to the limited channels applied to scan and generate the echo signals.

For these reasons, a need still exists for those of ordinary skill in the art to provide an improved method and system, particularly for 3D medical image scanning and display system to overcome such difficulties. Specifically, it is desirable to provide an improved method and configuration to improve the beam resolution and convenience of image construction for providing high quality and accurate images.

SUMMARY OF THE INVENTION

It is an aspect of the present invention to provide to new probe configuration and method to a medical image scanning system with techniques to improve the beam resolution and easy for probe production such that the above discussed limitations and difficulties may be resolved.

It is another aspect of the present invention to provide a new probe configuration and method to a medical image scanning system with techniques to more reliably and conveniently acquire a volume of multiple slices of two-dimensional image dataset without degrading the beam resolution and image quality.

It is another aspect of this invention by applying the concept of creating a phase delay profile for the transducer elements in azimuth dimension of the 2D image, while applying equal phase to the transducer elements in elevation dimension. By selecting the plural transducer elements in the elevation with linear or curve movement, the volume data can be acquired.

These and other objects and advantages of the present invention will no doubt become obvious to those of ordinary skill in the art after having read the following detailed description of the preferred embodiment, which is illustrated in the various drawing figures.

BRIEF DESCRIPTION OF FIGURES

The present invention is described in detail below with reference to the following Figures.

DESCRIPTION OF PREFERRED EMBODIMENTS

Figure 1A:
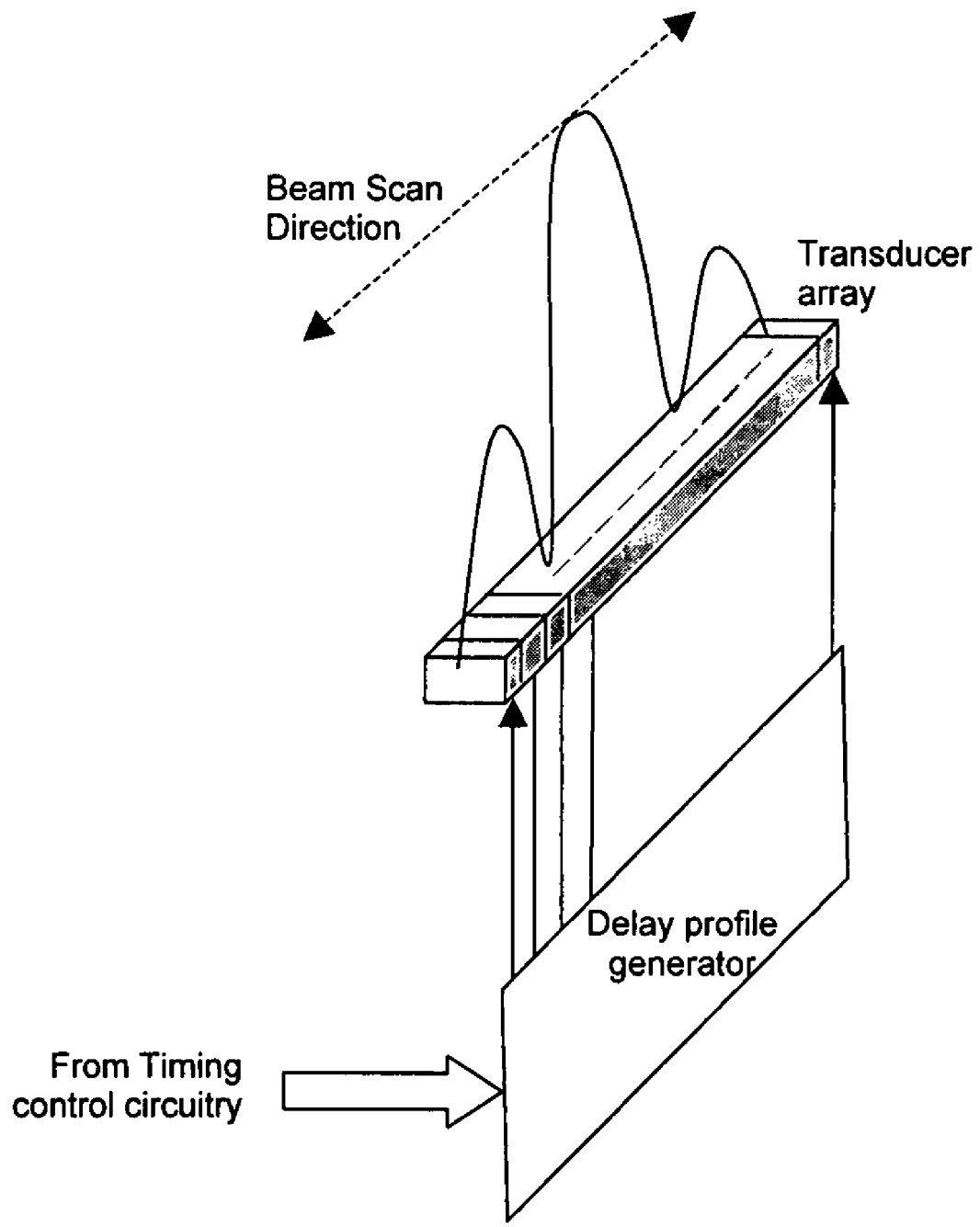
FIGS. 1A, 1B and 1C are schematic and functional diagrams for showing the beam profile configuration implemented in a conventional one-dimensional (1D) ultrasonic image probing system.
Figure 1B:
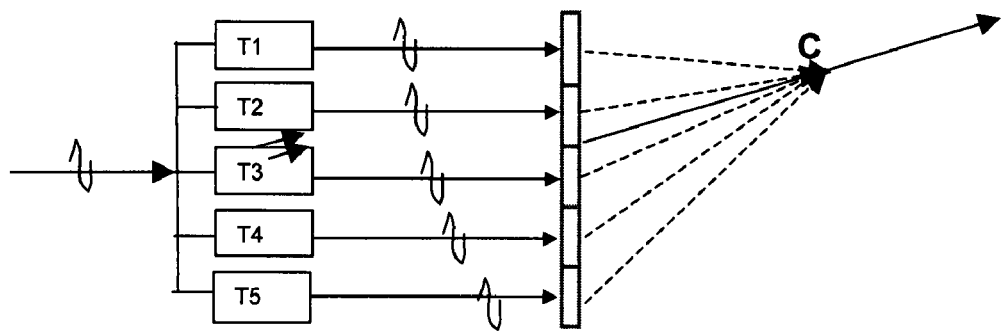
Figure 1C:
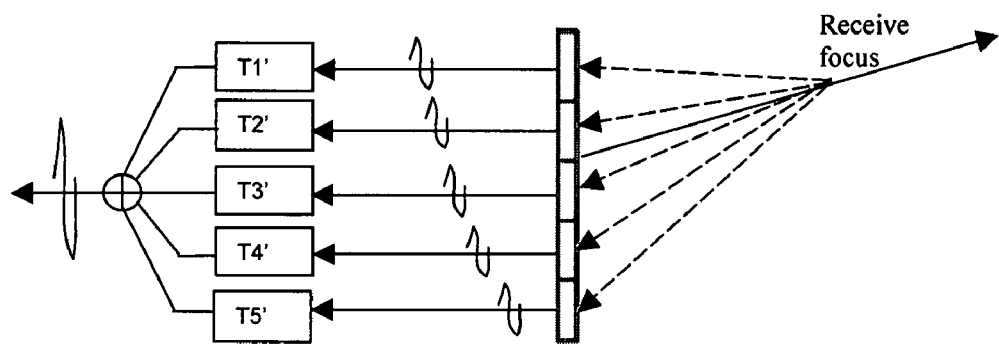
Figure 1D:
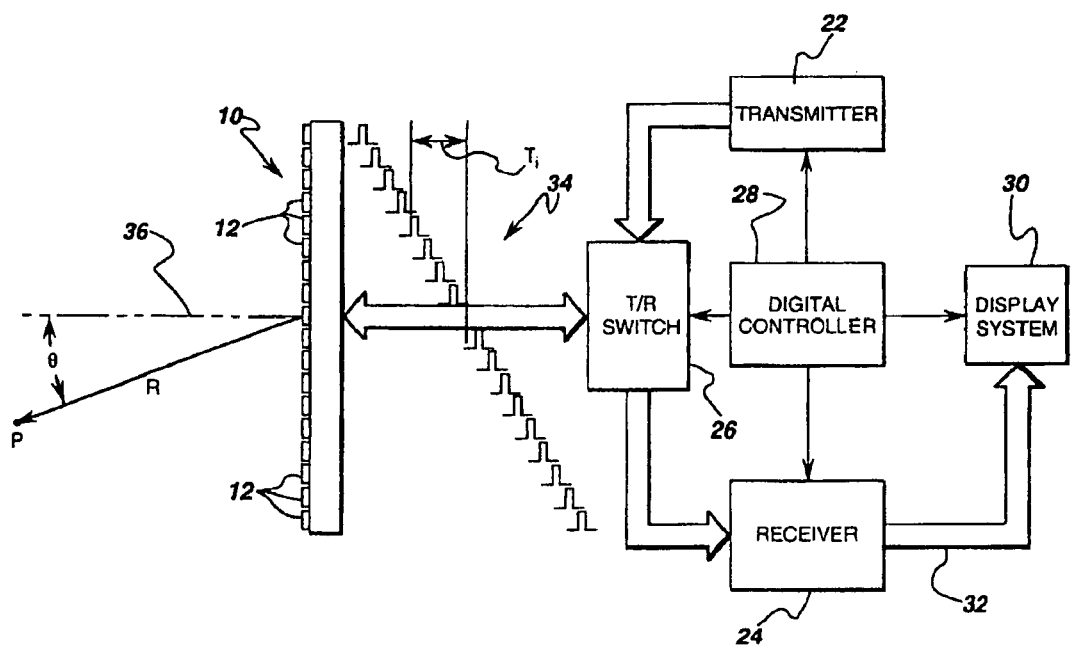
FIG. 1D is a functional block diagram for showing the system configuration and signal processing implemented in a conventional ultrasonic image probing system applying a two-dimensional (2D) sparse probe for 3-D scanning technique.
Figure 2:
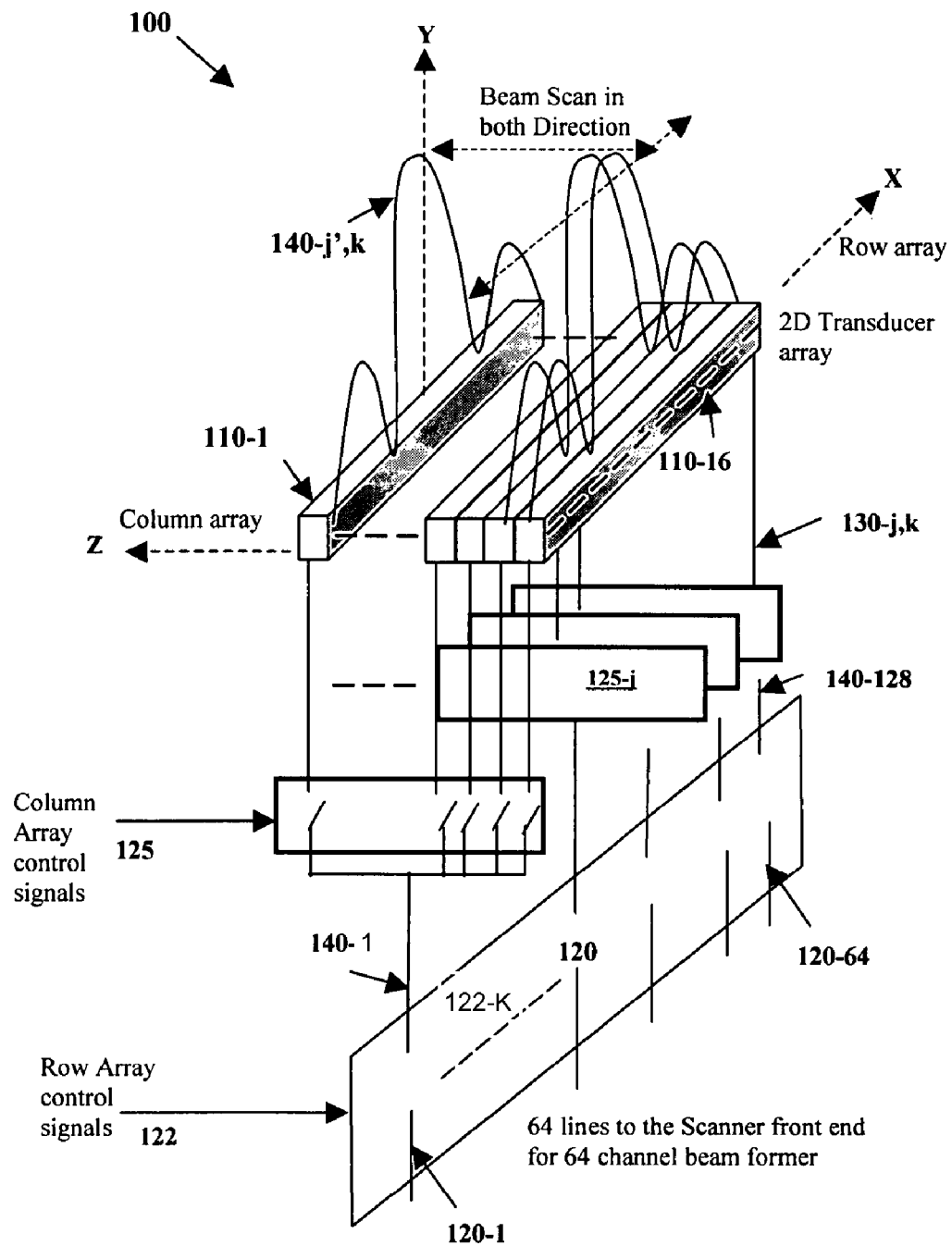
FIG. 2 is a perspective functional diagram for showing the beam profile and signal configuration of an equal phase two-dimensional ultrasonic probing system of this invention.

FIG. 2 is a perspective functional diagram of an equal phase two-dimensional (2D) ultrasonic probing system 100 of this invention. The 2D probing system includes sixteen column arrays 110 of probing transducers along the Z-axis direction. Each of these sixteen columns includes 128 probing transducers thus forming 128 rows of transducers along the X-axis direction. The probing system 100 further includes 64 lines 120-1 to 120-64 connected to the scanner front end for a 64-channel beam former to input the row-array control signals. Block 120 is a multiplexer which connects the selected 128-element bus (140-1 to 140-128) into 64-channel bus, e.g., 120-1 to 120-64. Each of these 64 lines 120-$i$ where $i$ =1 to 64, is further connected to one or more column array element 130-$j$, $k$ simultaneously through control lines 125-$j$ where j=1 to 128, and k=1 to 16. The set of column-array control lines 125 provide control signal that configures the column setting in real time. The column-array control lines 125-$j$ and row-array control signals transmitted through the row-array control lines 122-$k$ where k=1-128 provide control signals to energize the individual transducers to produce a burst of ultrasonic energy to project a waveform 140($j'$, $k$) where j'=1 to 128 and k=1 to 16. The ultrasonic energy produced from the transducers is projected out as waveforms and reflected back to the transducer array from the biological object under scanning investigation is converted into an electrical signal by the same transducers.

Figure 3:
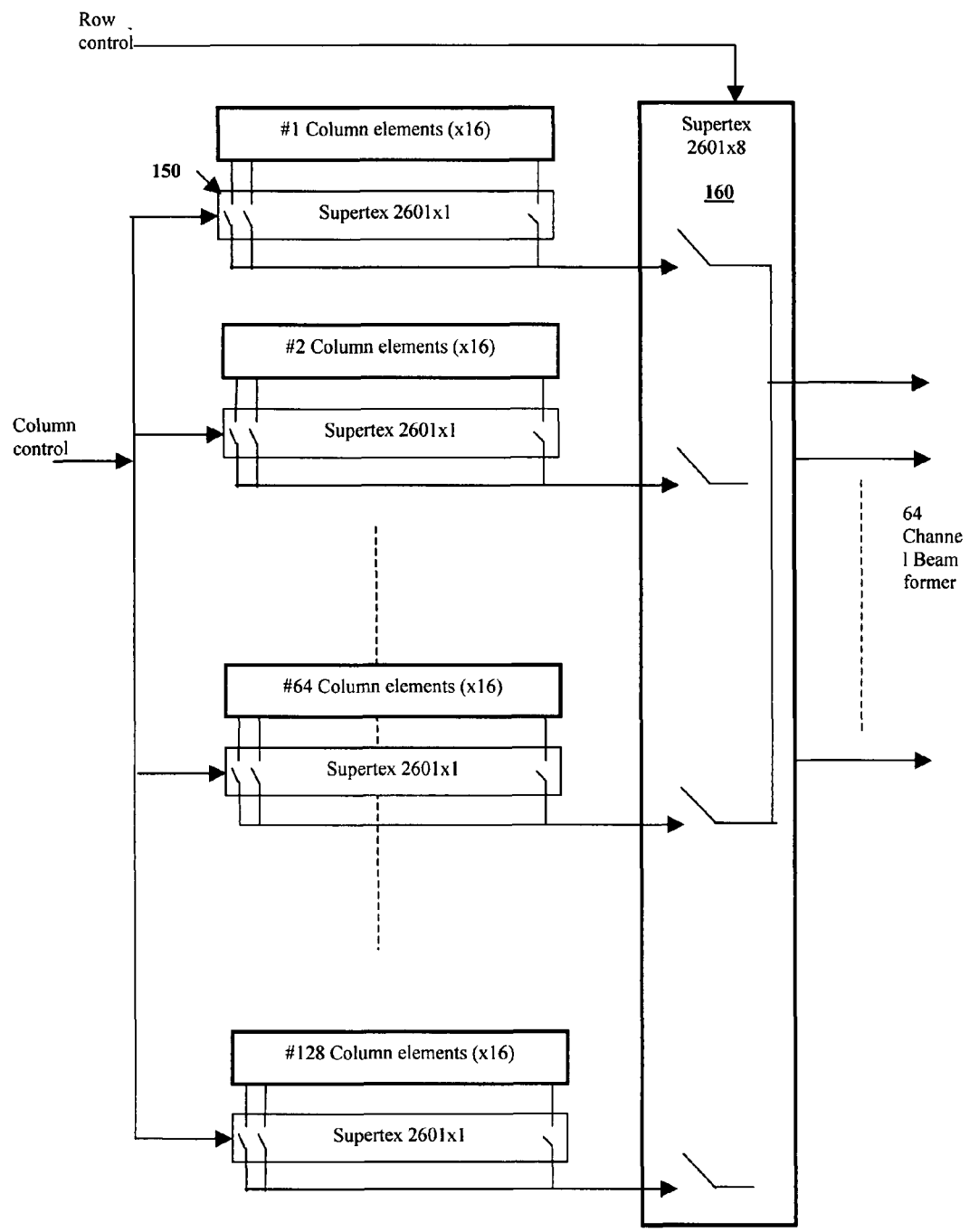
FIG. 3 is a schematic diagram for showing the concept of an element to channel connection of this invention to provide improved two-dimensional image resolutions and image constructions.

For the conventional approach, an ultrasonic probing system as shown in FIG. 2 would require a 128×16=2048 channel 2D beam formers. The system configuration and signal transmission and processing would be too complicated and almost impossible to implement. FIGS. 2 and 3 illustrate that the arrays of transducers are organized into column and row transducer elements. A 16-bit high voltage multiplexer 150, which acts as a switch and summer, sums one or several of the 16 column elements together and output as one row signal. Since the phase in the selected elevation elements are summed together with a flat delay profile, i.e., a uniform delay profile, the invention reduces the complexity of the 2D probe and system interface into practical implementation. The "Supertex 2601" from Supertex may be used and the control setting will connect and sum any number of the column elements together at the output with equal phase as shown in FIG. 3. For example, in acquiring the first slice 2D image of the 3D volume, the element number 1, 2 and 3 of the first column are all connected together, and the same for the $2^{nd}$ column and so on. The total of 128 row lines out of the column multiplexers 150 are connected to another level of row multiplexer 160 with 64 channel output, where these signals are treated as the conventional 1 D array to scan the beam for 2D image. In acquiring the $2^{nd}$ slice 2D image of the 3D volume, the column multiplexer controller set the output to have element number 2, 3 and 4 together, and the row multiplexer is controlled the same way as described before. Due to the physical transducer element location movement in the column direction, the 3D ultrasound volume data can be acquired.

The column controller can sum elements 1, 2 and 3 together first time with the beam center at element 2. It can also sum element 2 and 3 together to have beam center in the middle of element 2 and 3. This will produce a finer image at half pitch distance. In the curve linear array, the curvature can be maintain in both row and column direction to acquire a volume data with wider angle. In phase array, the beam will be steered in the row direction as the conventional approach while the column elements are controlled in the same way as the above description.

With this invention, the total multiplexers are reduced to 128+8=136 (128 16 bit multiplexer for column and 8 16 bit multiplexer for row decoding) for a 128×16 2D array, which is manageable to be fit into the probe scan-head. If the scanning system is configured to implement with 64 row element phase array probe, then the total number of high voltage multiplexer will be further reduced to 64+4=68.

With this invention, the biopsy under ultrasound imaging will be the most benefit due to the difficulty of maintaining the needle in parallel with the 2D image plane. Other 3D volume image such as tumor or baby face can also be utilized.

Figure 4:
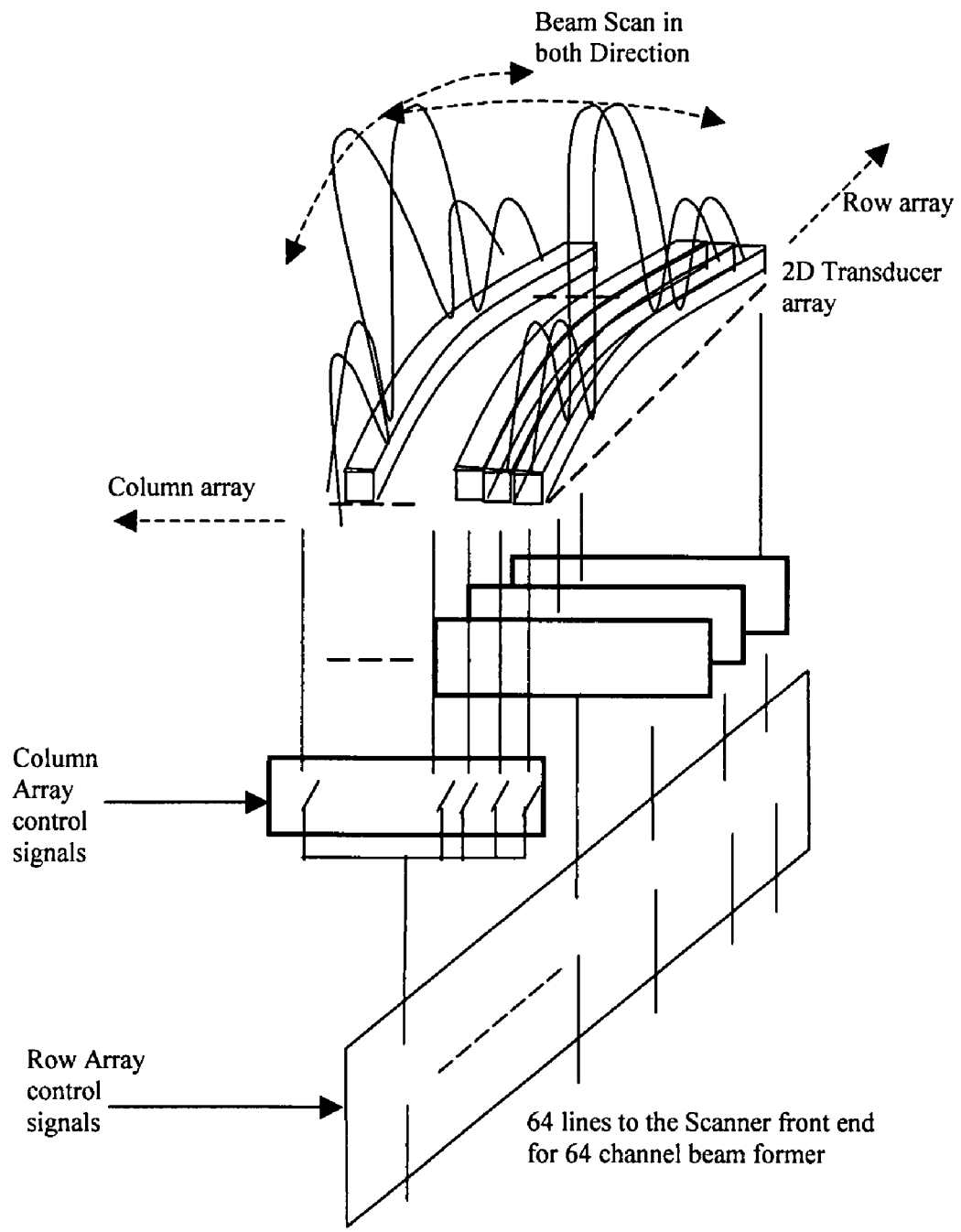
FIG. 4 is a perspective functional diagram for showing the beam profile and signal configuration of an equal phase two-dimensional ultrasonic probing system with curved transducer configuration of this invention.

The probe system shown in FIG. 4 is an alternate embodiment of the existing abdominal curve linear or small parts linear array probe in extra dimension with similar configurations as that shown in FIG. 2. The azimuth (or row) direction can have N elements (N is for instance from 64 to 256) and the Elevation (or column) plane can have M elements (for instance 8 to 128 elements). The probe can be seen as M pieces of 1D curve or linear array line up side by side with certain radius of curvature. The selection of the output from the elevation elements is controlled by the system. Only the adjacent L (L for example from 1 to M) elements in elevation dimension are tie together phase equally for imaging. It is similar to have a linear array with no electronic focusing in the elevation dimension. It relies on the geometry focusing when the transducer elements are placed According to above descriptions, this invention describes a medical image scanning system. The medical image scanning system includes a two-dimensional (2D) array probe constructed with transducer elements disposed in both azimuth and elevation dimension. The medical image scanning system further includes a multiplexer disposed along a first dimension for either one of the azimuth or the elevation dimension to route the transducer elements to system front end channels, and summing measurement signals from a designated number of the transducer elements along a second dimension into the first dimension. In an exemplary embodiment, the multiplexer further summing the measurement signals from the designated number of the transducer elements along the second dimension with a fixed phase delay profile into the first dimension. In another exemplary embodiment, the multiplexer further creating a fixed phase delay profile for summing the measurement signals from the designated number of the transducer elements along the second dimension by applying the fixed phase delay profile into the first dimension. In another exemplary embodiment, the multiplexer further creating a fixed phase delay profile equal to a focus at an infinite distance along the first dimension for summing the measurement signals from the designated number of the transducer elements along the second dimension by applying the fixed phase delay profile into the first dimension. When the focal point is at infinity, the delay profile for the elements in the aperture should be fixed with zero delay in between the elements. In another exemplary embodiment, the medical image scanning system further includes a scanner front end includes a channel beam former for inputting control signals to each of the transducer elements. In another exemplary embodiment, the medical image scanning system further includes a scanner front end includes a channel beam former for inputting azimuth and elevation control signals to each of the transducer elements configured as the 2D array. In another exemplary embodiment, the medical image scanning system further includes a scanner front end includes a channel beam former for inputting control signals to each of the transducer elements. The medical image scanning system further includes a channel signal multiplexer disposed between the channel beam former and the transducer elements for multiplexing the control signals generated from the channel beam former to the transducer elements. In another exemplary embodiment, the medical image scanning system further includes a second-dimension multiplexer for switching and summing measurement signals generated by the multiplexer disposed along the first dimension for generating measurement signals to acquire volume dataset for rendering a three-dimensional image. In another exemplary embodiment, the medical image scanning system further includes a second-dimension multiplexer for switching and summing measurement signals generated by the multiplexer disposed along the first dimension for generating measurement signals for rendering a three-dimensional image. The medical image scanning system further includes a total number of switching and summing circuits of the multiplexer along the first dimension and the second-dimension multiplexer is K+K*J wherein K is a total number of the transducer elements along the first dimension and J represents a total number of the transducer elements along the second dimension summed together with the fixed delay profile along the first dimension. With 16 switch/sum in one multiplexing package, the number of IC in 128×16 element transducer array will be (128+128*16)/16, which is 8+128 IC multiplexer chips. In another exemplary embodiment, the two-dimensional (2D) array probe constructed with transducer elements disposed in both azimuth and elevation dimension wherein a total number of transducer elements along either one of the azimuth and elevation dimension having a approximate range between four (4) to five hundred twelve (512) forming an array of preferably about N by M wherein 32>N>4 and 512>M>32.

According to above descriptions, this invention discloses a method for configuring a medical image scanning system. The method includes a step of constructing a two-dimensional (2D) array probe by disposing transducer elements in both azimuth and elevation dimension, The method further includes a step of disposing a multiplexer along a first dimension for either one of the azimuth or the elevation dimension for routing the transducer elements to system front end channels, and summing measurement signals from a designated number of the transducer elements along a second dimension into the first dimension. In an exemplary embodiment, the step of disposing the multiplexer further includes a step of summing the measurement signals from the designated number of the transducer elements along the second dimension with a fixed phase delay profile into the first dimension. In another exemplary embodiment, the step of disposing the multiplexer further includes a step of creating a fixed phase delay profile for summing the measurement signals from the designated number of the transducer elements along the second dimension by applying the fixed phase delay profile into the first dimension. In another exemplary embodiment, the step of disposing the multiplexer further includes a step of creating a fixed phase delay profile equal to a focus at an infinite distance along the first dimension for summing the measurement signals from the designated number of the transducer elements along the second dimension by applying the fixed phase delay profile into the first dimension. In another exemplary embodiment, the method further includes a step of connecting and applying a scanner front end with a channel beam former for inputting control signals to each of the transducer elements. In another exemplary embodiment, the method further includes a step of connecting and applying a scanner front end with a channel beam former for inputting azimuth and elevation control signals to each of the transducer elements configured as the 2D array. In another exemplary embodiment, the method further includes a step of connecting and applying a scanner front end with a channel beam former for inputting control signals to each of the transducer elements. And the method further includes another step of disposing a channel signal multiplexer between the channel beam former and the transducer elements for multiplexing the control signals generated from the channel beam former to the transducer elements. disposing a channel signal multiplexer between the channel beam former and the transducer elements for multiplexing the control signals generated from the channel beam former to the transducer elements connecting and applying a second-dimension multiplexer for switching and summing measurement signals generated by the multiplexer disposed along the first dimension for generating measurement signals to acquire volume dataset for rendering a three-dimensional image by disposing a channel signal multiplexer between the channel beam former and the transducer elements for multiplexing the control signals generated from the channel beam former to the transducer elements connecting and applying a second-dimension multiplexer for switching and summing measurement signals generated by the multiplexer disposed along the first dimension for generating measurement signals for rendering a three-dimensional image. The method further includes another step of arranging a total number of switching and summing circuits of the multiplexer along the first dimension and the second-dimension multiplexer is K+K·X·J wherein K is a total number of the transducer elements along the first dimension and J represents a total number of the transducer elements along the second dimension summed together with the fixed delay profile along the first dimension. In another exemplary embodiment, the step of constructing the two-dimensional (2D) array probe with transducer elements in both azimuth and elevation dimension further includes a step of arranging a total number of transducer elements along either one of the azimuth and elevation dimension having a approximate range between four (4) to five hundred twelve (512) forming an array of preferably about N by M wherein 32>N>4 and 512>M>32.

The description and the drawings of the present document describe examples of embodiment(s) of the present invention and also describe some exemplary optional feature(s) and/or alternative embodiment(s). It will be understood that the embodiments described are for the purpose of illustration and are not intended to limit the invention specifically to those embodiments. Rather, the invention is intended to cover all that is included within the spirit and scope of the invention, including alternatives, variations, modifications, equivalents, and the like.

We claim:

1. A medical image scanning system comprising:
   a two-dimensional (2D) array probe constructed with transducer elements disposed in both azimuth and elevation dimension;
   a multiplexer disposed along a first dimension for either one of said azimuth or said elevation dimension to route the transducer elements to system front end channels, and summing measurement signals from a designated number of said transducer elements along a second dimension into the first dimension, and the number of said transducer elements is designated by control signals, and said multiplexer further summing said measurement signals from said designated number of said transducer elements along said second dimension with a fixed phase delay profile into the first dimension;
   a second-dimension multiplexer for switching and summing measurement signals generated by said multiplexer disposed along said first dimension for generating measurement signals for rendering a three-dimensional image; and
   a total number of switching and summing circuits of said multiplexer along said first dimension and said second-dimension multiplexer is K+K*J wherein K is a total number of said transducer elements along said first dimension and J represents a total number of said transducer elements along said second dimension summed together with said fixed delay profile along said first dimension.

2. The medical image scanning system of claim 1 wherein:
   said multiplexer further creating the fixed phase delay profile for summing said measurement signals from said designated number of said transducer elements along said second dimension by applying said fixed phase delay profile into the first dimension.

3. The medical image scanning system of claim 1 wherein:
   said multiplexer further creating the fixed phase delay profile to be equal to a focus at an infinite distance along said first dimension for summing said measurement signals from said designated number of said transducer elements along said second dimension by applying said fixed phase delay profile into the first dimension.

4. The medical image scanning system of claim 1 further comprising:
   a scanner front end including a channel beam former for inputting control signals to each of said transducer elements.

5. The medical image scanning system of claim 1 further comprising:
   a scanner front end including a channel beam former for inputting azimuth and elevation control signals to each of said transducer elements configured as said 2D array.

6. The medical image scanning system of claim 1 further comprising:
   a scanner front end including a channel beam former for inputting control signals to each of said transducer elements; and
   a channel signal multiplexer disposed between said channel beam former and said transducer elements for multiplexing said control signals generated from said channel beam former to said transducer elements.

7. The medical image scanning system of claim 1 wherein:
   the second-dimension multiplexer for switching and summing measurement signals generated by said multiplexer disposed along said first dimension for generating measurement signals for rendering a three-dimensional image comprises:
   a second-dimension multiplexer for switching and summing measurement signals generated by said multiplexer disposed along said first dimension for generating measurement signals to acquire volume dataset for rendering a three-dimensional image.

8. The medical image scanning system of claim 1 wherein:
   said two-dimensional (2D) array probe constructed with transducer elements disposed in both azimuth and elevation dimension wherein a total number of transducer elements along either one of said azimuth and elevation dimension having a approximate range between four (4) to five hundred twelve (512) forming an array of preferably about N by M wherein 32>N>4 and 512>M>32.

9. A method for configuring a medical image scanning system comprising:
   constructing a two-dimensional (2D) array probe by disposing transducer elements in both azimuth and elevation dimension;
   disposing a multiplexer along a first dimension for either one of said azimuth or said elevation dimension for routing the transducer elements to system front end channels, and summing measurement signals from a designated number of said transducer elements along a second dimension into the first dimension, and the number of said transducer elements is designated by control signals, and the step of disposing said multiplexer further comprising a step of summing said measurement signals from said designated number of said transducer elements along said second dimension with a fixed phase delay profile into the first dimension;
   connecting and applying a second-dimension multiplexer for switching and summing measurement signals generated by said multiplexer disposed along said first dimension for generating measurement signals for rendering a three-dimensional image; and
   arranging a total number of switching and summing circuits of said multiplexer along said first dimension and said second-dimension multiplexer is K+K*J wherein K is a total number of said transducer elements along said first dimension and J represents a total number of said transducer elements along said second dimension summed together with said fixed delay profile along said first dimension.

10. The method of claim 9 wherein:
    the step of disposing said multiplexer further comprising a step of creating the fixed phase delay profile to be for summing said measurement signals from said designated number of said transducer elements along said second dimension by applying said fixed phase delay profile into the first dimension.

11. The method of claim 9 wherein:
    the step of disposing said multiplexer further comprising a step of creating the fixed phase delay profile equal to a focus at an infinite distance along said first dimension for summing said measurement signals from said designated number of said transducer elements along said second dimension by applying said fixed phase delay profile into the first dimension.

12. The method of claim 9 further comprising:
connecting and applying a scanner front end with a channel beam former for inputting control signals to each of said transducer elements.

13. The method of claim 9 further comprising:
connecting and applying a scanner front end with a channel beam former for inputting azimuth and elevation control signals to each of said transducer elements configured as said 2D array.

14. The method of claim 9 further comprising:
connecting and applying a scanner front end with a channel beam former for inputting control signals to each of said transducer elements; and
disposing a channel signal multiplexer between said channel beam former and said transducer elements for multiplexing said control signals generated from said channel beam former to said transducer elements.

15. The method of claim 9 wherein:
connecting and applying a second-dimension multiplexer for switching and summing measurement signals generated by said multiplexer disposed along said first dimension for generating measurement signals for rendering a three-dimensional image comprises:
connecting and applying a second-dimension multiplexer for switching and summing measurement signals generated by said multiplexer disposed along said first dimension for generating measurement signals to acquire volume dataset for rendering a three-dimensional image.

16. The method of claim 9 wherein:
the step of constructing said two-dimensional (2D) array probe with transducer elements in both azimuth and elevation dimension further comprising a step of arranging a total number of transducer elements along either one of said azimuth and elevation dimension having a approximate range between four (4) to five hundred twelve (512) forming an array of preferably about N by M wherein 32>N>4 and 512>M>32.

\* \* \* \* \*